US012539415B2

(12) United States Patent
Yun et al.

(10) Patent No.: US 12,539,415 B2
(45) Date of Patent: Feb. 3, 2026

(54) HIGH FREQUENCY TREATMENT HANDPIECE HAVING ROLLER ELECTRODES

(71) Applicant: DAEYANG MEDICAL CO., LTD., Wonju-si (KR)

(72) Inventors: Jeong-Sub Yun, Wonju-si (KR); Kwang Seok Seo, Wonju-si (KR)

(73) Assignee: DAEYANG MEDICAL CO., LTD., Wonju-si (KR)

( * ) Notice: Subject to any disclaimer, the term of this patent is extended or adjusted under 35 U.S.C. 154(b) by 864 days.

(21) Appl. No.: 17/641,355

(22) PCT Filed: Jul. 8, 2020

(86) PCT No.: PCT/KR2020/008901
§ 371 (c)(1),
(2) Date: Mar. 8, 2022

(87) PCT Pub. No.: WO2021/075670
PCT Pub. Date: Apr. 22, 2021

(65) Prior Publication Data

US 2022/0339438 A1 Oct. 27, 2022

(30) Foreign Application Priority Data

Oct. 18, 2019 (KR) ........................ 10-2019-0129968

(51) Int. Cl.
*A61N 1/06* (2006.01)
*A61F 7/00* (2006.01)
(Continued)

(52) U.S. Cl.
CPC ................ *A61N 1/06* (2013.01); *A61F 7/007* (2013.01); *A61H 15/02* (2013.01); *A61N 1/328* (2013.01);
(Continued)

(58) Field of Classification Search
CPC .......................... A61N 1/06; A61B 2018/0016
See application file for complete search history.

(56) References Cited

U.S. PATENT DOCUMENTS 5,843,152 A * 12/1998 Tu ............................ A61N 1/06 606/41
6,662,054 B2 * 12/2003 Kreindel ............ A61B 18/1402 607/101
(Continued)

FOREIGN PATENT DOCUMENTS

JP 2014-113272 A 6/2014
KR 10-2013-0005126 A 1/2013
(Continued)

OTHER PUBLICATIONS

International Search Report dated Apr. 5, 2021, issued in counterpart International Application No. PCT/KR2020/008901. w/English Translation. (7 pages).

*Primary Examiner* — Linda C Dvorak
*Assistant Examiner* — Ryan T Clark
(74) *Attorney, Agent, or Firm* — WHDA, LLP

(57) ABSTRACT

Disclosed is a high frequency treatment handpiece having roller electrodes. The handpiece includes: a handpiece casing part; and a plurality of roller electrode members rotatably positioned on a lower surface of the handpiece casing part and applying a high frequency by being brought into contact with the skin. The handpiece prevents burning when the continuous rubbing of a treated area is performed during a treatment, allows a practitioner to conveniently perform the treatment, and allows a person being treated to comfortably receive the treatment with minimum pain. Ball electrodes and roller electrodes can be selectively used, and a roller fixed mode, which limits the rotation of the roller electrodes, can also be selectively used, and thus various massage effects can be selectively provided in accordance
(Continued)

with the condition of a patient's skin, and the effect of the high frequency treatment can be maximized by means of the various massage effects.

9 Claims, 9 Drawing Sheets

(51) Int. Cl.

| | |
|---|---|
| ***A61H 15/02*** | (2006.01) |
| ***A61N 1/32*** | (2006.01) |
| ***A61N 1/40*** | (2006.01) |
| *A61H 15/00* | (2006.01) |

(52) U.S. Cl.

CPC ...... *A61N 1/403* (2013.01); *A61F 2007/0075* (2013.01); *A61F 2007/0087* (2013.01); *A61H 2015/0042* (2013.01); *A61H 2201/0285* (2013.01); *A61H 2201/10* (2013.01)

(56) References Cited

U.S. PATENT DOCUMENTS

| | | | | |
|---|---|---|---|---|
| 9,872,813 | B2 * | 1/2018 | Giraud | A61H 7/005 |
| 10,137,054 | B2 | 11/2018 | Giraud et al. | |
| 2008/0183251 | A1 * | 7/2008 | Azar | A61B 18/14<br>607/101 |
| 2010/0145242 | A1 | 6/2010 | Tsai | |
| 2014/0142472 | A1 | 5/2014 | Giraud et al. | |
| 2015/0305969 | A1 | 10/2015 | Giraud et al. | |
| 2016/0100852 | A1 * | 4/2016 | Hyde | A61B 5/0077<br>600/309 |

FOREIGN PATENT DOCUMENTS

| | | | |
|---|---|---|---|
| KR | 10-2015-0086512 | A | 7/2015 |
| KR | 10-1984475 | B1 | 9/2019 |

* cited by examiner

HIGH FREQUENCY TREATMENT HANDPIECE HAVING ROLLER ELECTRODES

TECHNICAL FIELD

The present disclosure relates generally to a high frequency treatment handpiece having roller electrodes and, more particularly, to a high frequency treatment handpiece having roller electrodes that are rotated in contact with the skin.

BACKGROUND ART

A high frequency current generally refers to an alternating current having a frequency of more than 100,000 Hz, and is characterized by a small oscillation amplitude, so that no electrochemical reaction or electrolysis phenomenon occurs, and oscillating current energy is converted into thermal energy only within a predetermined path.

In particular, when the high frequency current passes through human tissue, it hardly causes ion movement and causes no electrochemical reaction or electrolysis phenomenon because the oscillation amplitude is very small.

When the high frequency current is applied to the tissue, whenever the current changes the direction thereof, the molecules that make up the tissue vibrate and rub against each other, generating biological thermal energy.

In addition, unlike other current types, the high frequency current does not stimulate the sensory and motor nerves, does not cause inconvenience or muscular contraction, and generates thermal energy. This thermal energy can also provide additional effects of enhancing cell function and increasing blood flow.

For this reason, treatment devices using high frequency current are used for various therapeutic purposes such as skin rejuvenation, skin lifting, suppression of melanin secretion, obesity treatment, skin care, hair promotion, pain relief, etc.

An example of conventional high-frequency treatment devices includes a handpiece for high-frequency treatment provided with a high-frequency electrode to which a high frequency current is applied in contact with a treated area of the skin, and a body having a high-frequency generator that receives power and supplies a high frequency current to the handpiece and a high-frequency operation controller that controls the operation of the high-frequency generator. The handpiece is configured in a form electrically connected to the body by a cable or the like.

The handpiece for high-frequency treatment is provided with a flat electrode part or can only make contact with the skin at one point through a spherical fixed electrode.

As a result, the handpiece for high-frequency treatment is problematic in that the heat is accumulated in a local area of the skin during high-frequency output from the electrode, causing burning.

In addition, the handpiece for high-frequency treatment repeatedly performs the action of continuously rubbing the treated area during the treatment in order to increase the massage effect when used. In this case, friction is generated between the skin and the fixed electrode, causing unnecessary fatigue and pain for both a practitioner and a patient.

In addition, the handpiece for high-frequency treatment is limited in the treatment method due to the use of the fixed electrode, so that it is difficult to expect an increase in the treatment effect through various massage effects according to the skin condition of patients.

DISCLOSURE

Technical Problem

Accordingly, the present disclosure has been made keeping in mind the above problems occurring in the related art, and an objective of the present disclosure is to provide a high frequency treatment handpiece having roller electrodes that are rotated in contact with the skin, the handpiece being capable of preventing burning when the continuous rubbing of a treated area is performed during a treatment, allowing a practitioner to conveniently perform the treatment, and allows a person being treated to comfortably receive the treatment with minimum pain.

Another objective of the present disclosure is to provide a high frequency treatment handpiece having roller electrodes, in which ball electrodes and roller electrodes can be selectively used, and a roller fixed mode, which limits the rotation of the roller electrodes, can also be selectively used, and thus various massage effects can be selectively provided in accordance with the condition of a patient's skin.

Technical Solution

In order to accomplish the above objectives, an aspect of the present disclosure provides a high frequency treatment handpiece having roller electrodes, the high frequency treatment handpiece including: a handpiece casing part; and a plurality of roller electrode members rotatably positioned on a lower surface of the handpiece casing part and configured to apply a high frequency by being brought into contact with the skin of a patient.

The high frequency treatment handpiece may further include: a ball electrode part positioned to be movable upward and downward in the handpiece casing part and having a ball electrode member that protrudes from a lower surface thereof, configured to be rolled in contact with the skin, and configured to apply a high frequency; and an electrode lifting part configured to move the ball electrode part upward and downward.

The ball electrode part may be positioned to protrude from the lower surface of the handpiece casing part so that the ball electrode member is positioned to protrude to a height equal to or lower than a height of the roller electrode members, whereby when the roller electrode members are brought into contact with the skin, the ball electrode member may be brought into contact with the skin simultaneously with the roller electrode members and be rolled in contact with the skin to generate a massage effect on the skin.

The ball electrode member may be positioned to protrude from the lower surface of the handpiece casing part so that when the ball electrode member is brought into contact with the skin simultaneously with the roller electrode members, the ball electrode member may be in a state in which the supply of electric power is cut off.

The electrode lifting part may include a stopper panel connected to the ball electrode part, positioned to be spaced apart from an upper portion of the handpiece casing part, and configured to limit a maximum protrusion height of the ball electrode part. The maximum protrusion height of the ball electrode part limited by the stopper panel may be a height at which only the ball electrode member applies the high frequency by being brought into contact with the skin while the roller electrode members are not brought into contact with the skin.

A first ball electrode power application terminal configured to apply electric power to the ball electrode part may be positioned on a lower surface of the stopper panel, and a second ball electrode power application terminal electrically connected to the first ball electrode power application terminal and configured to apply electric power to the ball electrode part may be positioned on an upper surface of the handpiece casing part. When the ball electrode part protrudes to the maximum protrusion height from the lower surface of the handpiece casing part as the stopper panel is seated on the upper surface of the handpiece casing part, the ball electrode part may apply the high frequency to the skin through electrical connection between the first and second ball electrode power application terminals.

Advantageous Effects

By the provision of roller electrodes that are rotated in contact with the skin, the present disclosure prevents burning when the continuous rubbing of a treated area is performed during a treatment, allows a practitioner to conveniently perform the treatment, and allows a person being treated to comfortably receive the treatment with minimum pain.

Ball electrodes and roller electrodes can be selectively used, and a roller fixed mode, which limits the rotation of the roller electrodes, can also be selectively used. Thus, various massage effects can be selectively provided in accordance with the condition of a patient's skin, and the effect of the high frequency treatment can be maximized by means of the various massage effects.

Figure 1:
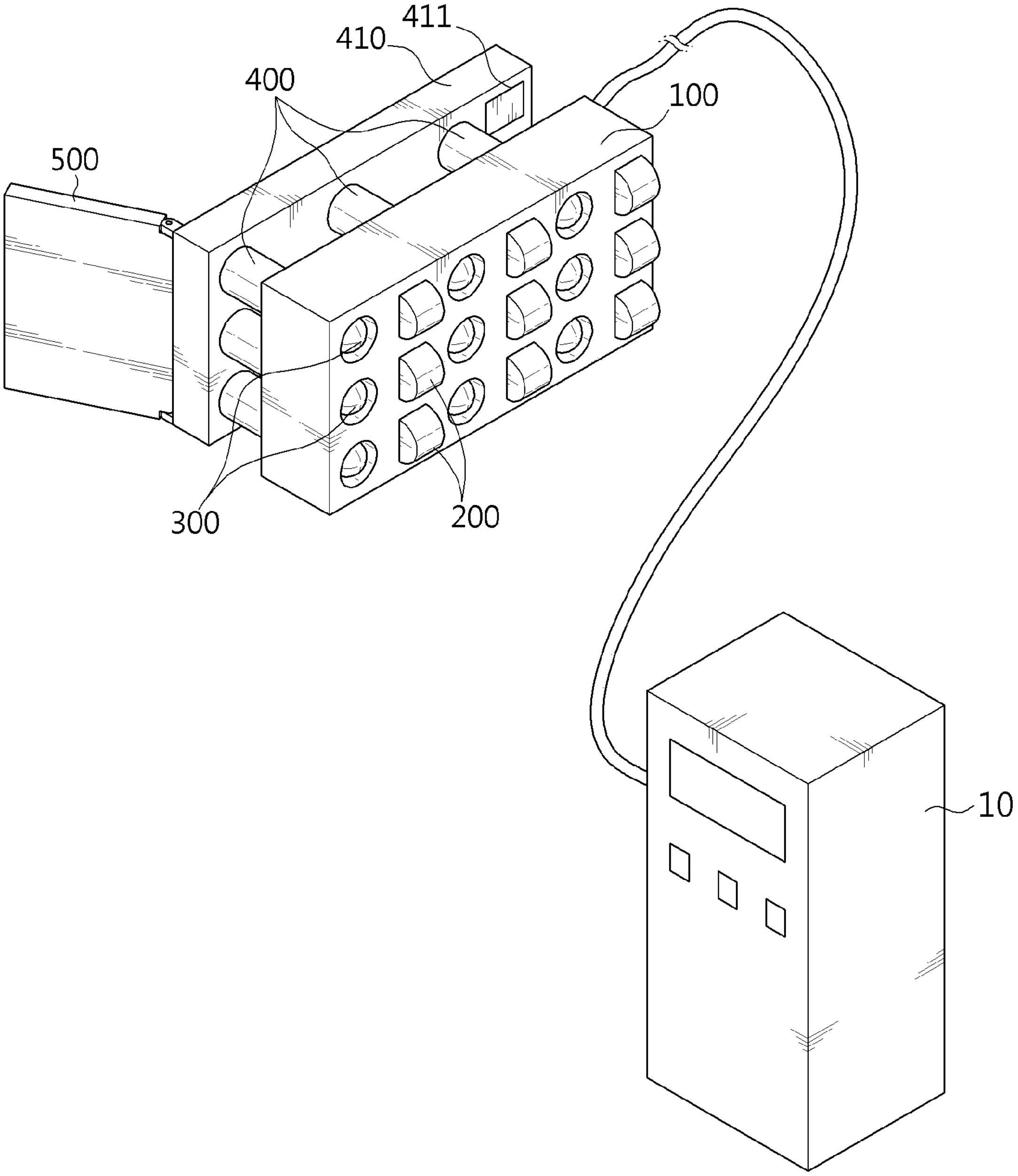
FIGS. 1 to 3 are perspective views illustrating an embodiment of a high frequency treatment handpiece having roller electrodes according to the present disclosure.

*Description of the Reference Numerals in the Drawings*

| | |
|---|---|
| 100: handpiece casing part | 200: roller electrode member |
| 210: hollow hole | 300: ball electrode part |
| 310: ball electrode housing member | 320: ball electrode member |
| 400: electrode lifting part | 410: stopper panel |
| 411: first ball electrode power application terminal | 412: second ball electrode power application terminal |
| 500: display panel part | 600: ratchet part |
| 610: ratchet wheel member | 620: pole member |
| 630: brush terminal | 700: rotation detection sensor |
| 800: pressure sensor | |

BEST MODE

The present disclosure will be described in more detail.

Reference will now be made in detail to an exemplary embodiment of the present disclosure with reference to the accompanying drawings. Prior to the description, it should be understood that all terms or words used in the specification and claims have the same meaning as commonly understood by one of ordinary skill in the art to which inventive concepts belong. Therefore, the description proposed herein is just a preferable example for the purpose of illustrations only, not intended to limit the scope of the disclosure, so it should be understood that other equivalents and modifications could be made thereto without departing from the spirit and scope of the disclosure.

Figure 2:
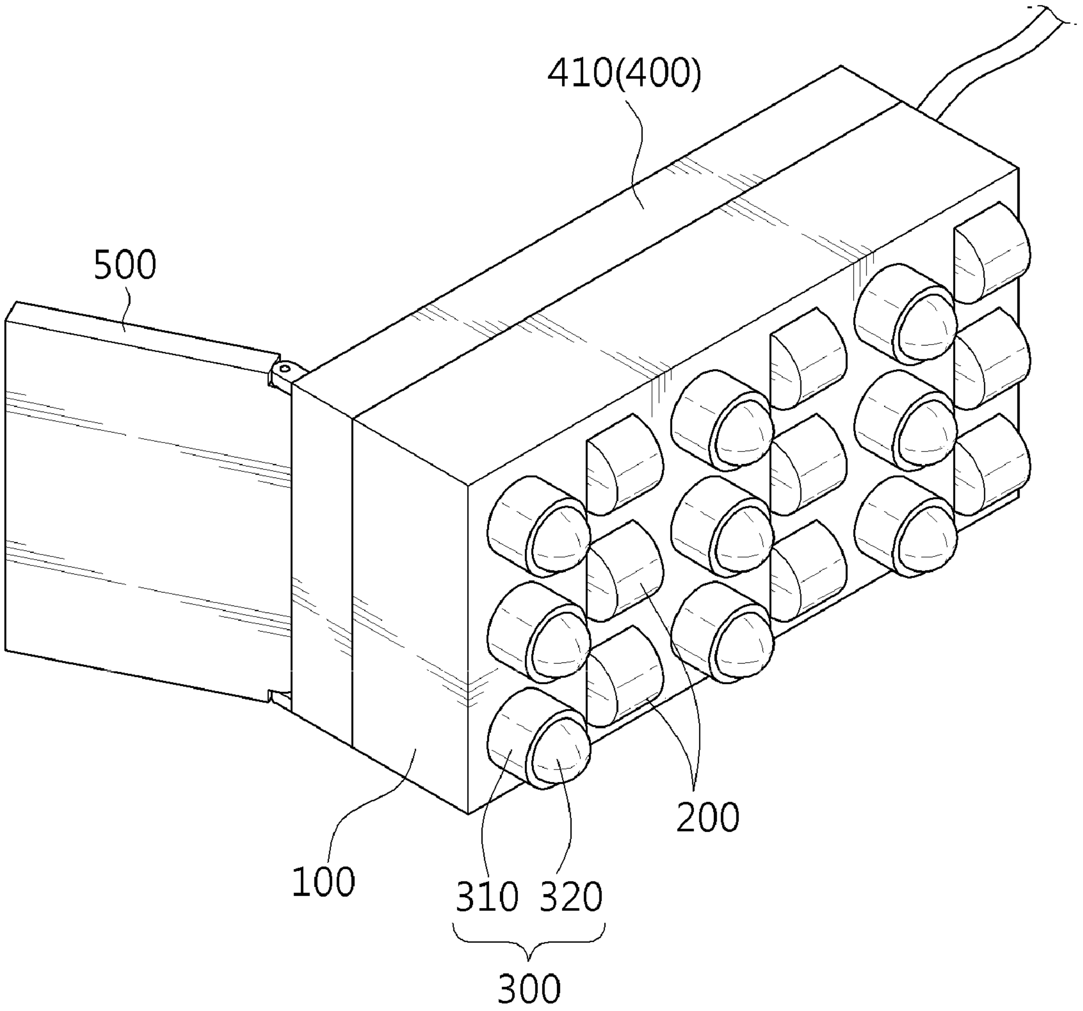
Figure 3:
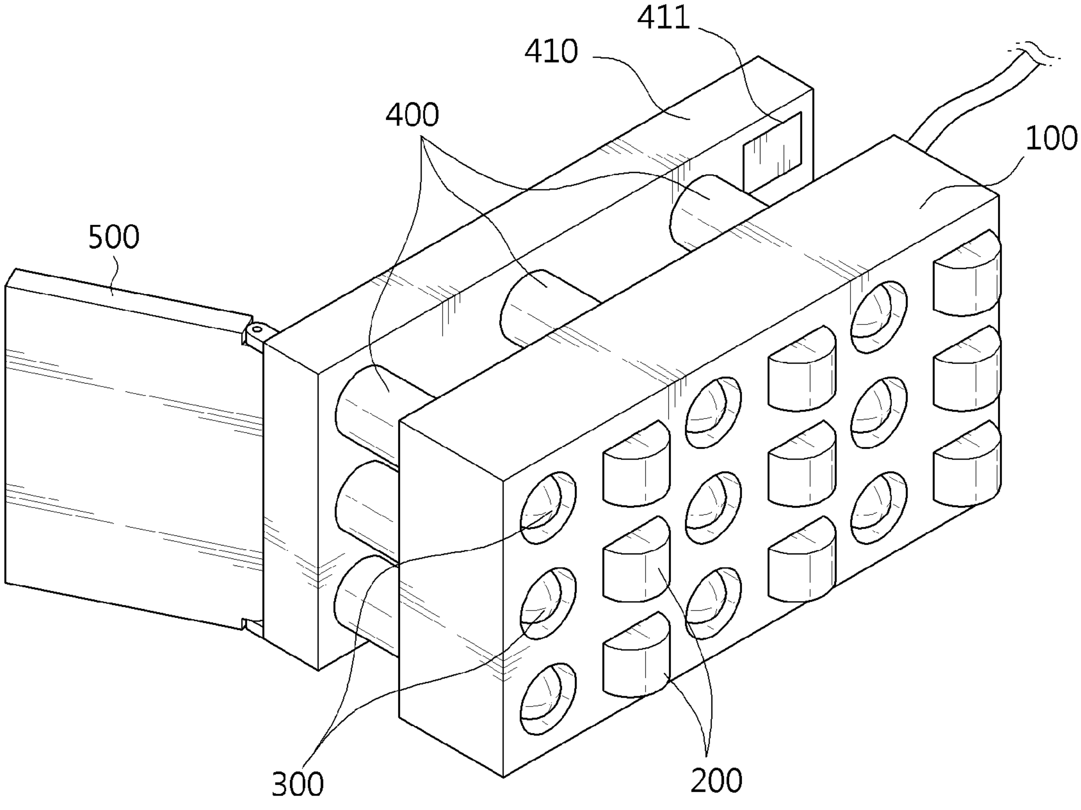
Figure 4:
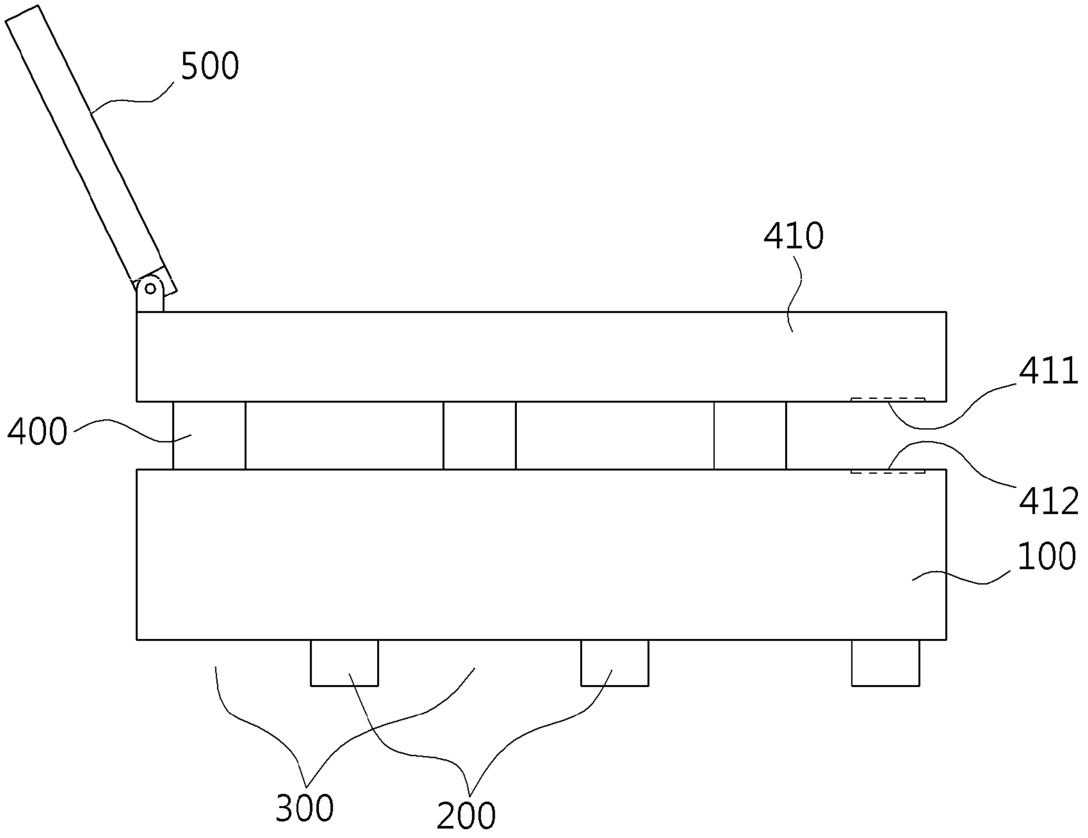
FIGS. 4 and 5 are front views illustrating the embodiment of the high frequency treatment handpiece having roller electrodes according to the present disclosure.
Figure 5:
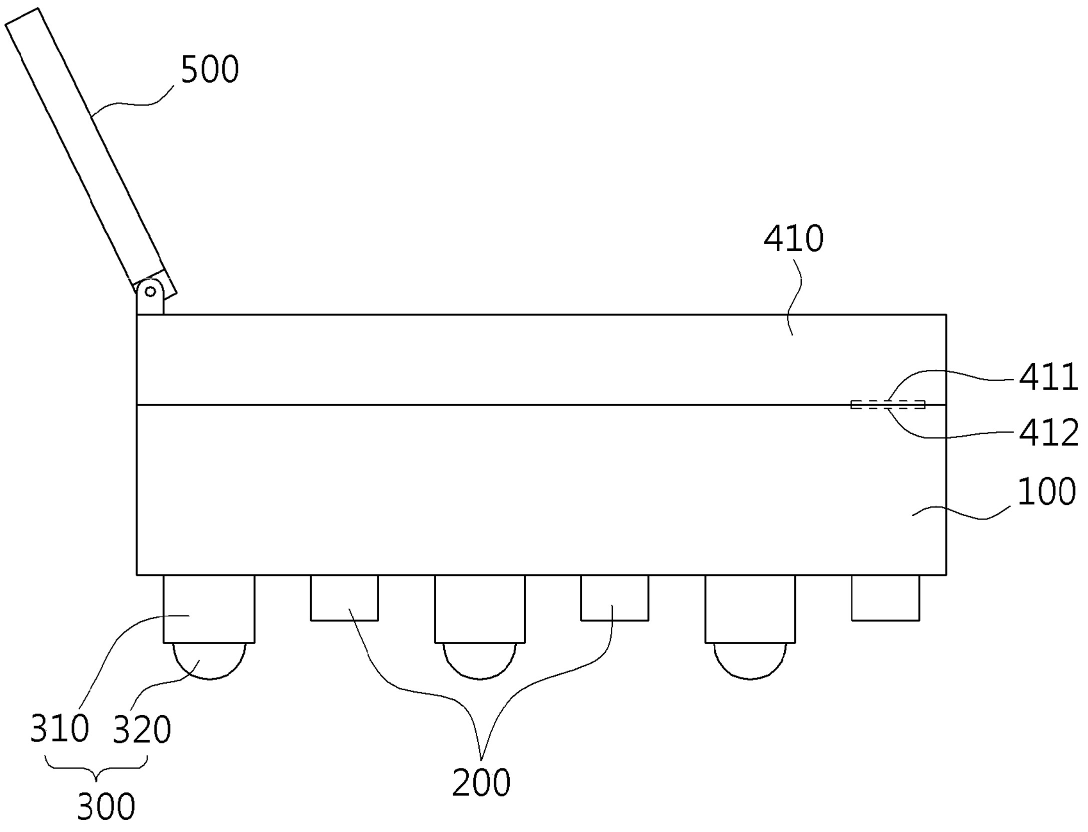

FIGS. 1 to 3 are perspective views illustrating an embodiment of a high frequency treatment handpiece having roller electrodes according to the present disclosure. FIGS. 4 and 5 are front views illustrating the embodiment of the high frequency treatment handpiece having roller electrodes according to the present disclosure.

The embodiment of the high frequency treatment handpiece having roller electrodes according to the present disclosure will be described in detail below with reference to FIGS. 1 to 4.

The embodiment of the high frequency treatment handpiece having roller electrodes according to the present disclosure includes a handpiece casing part 100.

The handpiece casing part 100 is connected to a high frequency treatment body 10 having a high frequency generator that receives power and supplies a high frequency current to the handpiece and a high frequency operation controller that controls the operation of the high frequency generator.

The high frequency treatment body 10 may be a body structure that controls the operation of the high frequency treatment handpiece in a known high frequency treatment device, but the present disclosure is not limited thereto. Various other body structures may also be used and a more detailed description thereof is omitted.

A plurality of roller electrode members 200 are rotatably positioned on a lower surface of the handpiece casing part 100.

The roller electrode members 200 may be positioned to be rotatable in the left and right directions or may be positioned to be rotatable in the front and rear directions, but the present disclosure is not limited thereto. For example, the roller electrode members 200 may be positioned to be rotatable in one direction.

The roller electrode members 200 are high frequency electrodes that apply a high frequency by being brought into contact with the skin of a person being treated, i.e., a patient.

Each of the roller electrode members 200 partially protrudes from the lower surface of the handpiece casing part 100 and is mounted on the handpiece casing part 100 so as to be rotatable about a roller shaft.

The roller electrode member 200 may have a structure that can be rotated while receiving electric power through an electric wire connected to the center of rotation of the roller shaft, or may receive electric power by maintaining a state in which an outer circumferential surface thereof is in elastic contact with a brush electrode.

The roller electrode member 200 generates a high frequency by receiving electric power from the high frequency treatment body 10 through a known mechanism for supplying electric power to a rotating body.

The embodiment of the high frequency treatment handpiece having roller electrodes according to the present disclosure may further include: a ball electrode part 300 positioned to be movable upward and downward in the handpiece casing part 100 and having a ball electrode member 320 that protrudes from a lower surface thereof, is rolled in contact with the skin, and applies a high frequency; and an electrode lifting part 400 moving the ball electrode part 300 upward and downward.

The ball electrode part 300 includes a ball electrode housing member 310 positioned to be movable upward and downward in the handpiece casing part 100, and the ball electrode member 320 rotatably positioned under the ball electrode housing member 310 and protruding from a lower portion of the ball electrode housing member 310.

The ball electrode part 300 may receive electric power by maintaining a state in which a brush electrode is in elastic contact with an outer circumferential surface of the ball electrode member 320 inside the ball electrode housing member 310.

The ball electrode member 320 is a high frequency electrode that applies a high frequency by being brought into contact with the skin of the person being treated, i.e., the patient, and generates a high frequency by receiving electric power through a known mechanism for supplying electric power to a rotating body.

Each of the roller electrode member 200 and the ball electrode member 320 is, for example, a capacity electric transfer (CET) type electrode or a resistive electric transfer (RET) type electrode.

The electrode lifting part 400 may be a hydraulic cylinder, but the present disclosure is not limited thereto. For example, the electrode lifting part 400 may be other known linear reciprocating devices such as a rack pinion structure using a pinion gear rotated by a motor and a rack gear meshing with the pinion gear, a ball screw type linear actuator, etc.

The ball electrode member 320 protrudes from a lower surface of the ball electrode housing member 310 and is rotatably positioned so as to be freely rotated in a 360 degree radius by being brought into contact with the skin.

The ball electrode part 300 is positioned at a lower height than the roller electrode members 200 with respect to the lower surface of the handpiece casing part 100.

The ball electrode part 300 may be positioned in a state inserted into the handpiece casing part 100 so as not to be brought into contact with the skin when a treatment is performed with the roller electrode members 200.

In addition, the ball electrode part 300 may be positioned so that the ball electrode member 320 protrudes from the lower surface of the handpiece casing part 100. Thus, when the roller electrode member 200 performs the treatment by applying a high frequency to the skin, the ball electrode member 320 may be rotated in contact with the skin to generate a massage effect on the skin.

The ball electrode member 320 may protrude to a height equal to that of the roller electrode members 200. Thus, when the roller electrode members 200 are brought into contact with the skin, the ball electrode member 320 may be rolled in contact with the skin to generate a massage effect on the skin, thereby improving a therapeutic effect.

In this case, no electric power is applied to the ball electrode member 320, and the ball electrode member 320 provides only a massage effect while being simply rolled in contact with the skin.

In a case where both the roller electrode members 200 and the ball electrode member 320 receive electric power and simultaneously apply a high frequency to the skin, burning may be caused in a treated area of the skin and excessive heat may cause damage to the skin.

To overcome such a problem, when the ball electrode member 320 and the roller electrode members 200 are simultaneously brought into contact with the skin, the supply of the electric power to the ball electrode member 320 is cut off so that only the roller electrode members 200 apply the high frequency to the skin.

In addition, the ball electrode part 300 may protrude to a height higher than that the roller electrode members 200 with respect to the lower surface of the handpiece casing part 100. Thus, only the ball electrode member 320 may apply the high frequency by being brought into contact with the skin while the roller electrode members 200 are not brought into contact with the skin.

The electrode lifting part 400 may include a stopper panel 410 connected to the ball electrode housing member 310, positioned to be spaced apart from an upper portion of the handpiece casing part 100, and limiting a maximum protrusion height of the ball electrode part 300.

The maximum protrusion height of the ball electrode part 300 limited by the stopper panel 410 is a height at which only the ball electrode member 320 applies the high frequency by being brought into contact with the skin while the roller electrode members 200 are not brought into contact with the skin.

A first ball electrode power application terminal 411 applying electric power to the ball electrode part 300 is positioned on a lower surface of the stopper panel 410. A second ball electrode power application terminal 412 electrically connected to the first ball electrode power application terminal 411 to apply electric power to the ball electrode part 300 is positioned on an upper surface of the handpiece casing part 100.

The ball electrode part 300 applies the high frequency to the skin by receiving electric power only when the ball electrode part 300 protrudes to a maximum height from the lower surface of the handpiece casing part 100 as the stopper panel 410 is seated on the upper surface of the handpiece casing part 100.

When the first ball electrode power application terminal 411 and the second ball electrode power application terminal 412 are electrically connected to each other, the supply of the electric power to the roller electrode members 200 is automatically cut off so that the electric power is supplied only to the ball electrode part 300.

Due to the fact that the ball electrode part 300 applies the high frequency to the skin by receiving the electric power only when it protrudes to the maximum protrusion height from the lower surface of the handpiece casing part 100, in a case where the ball electrode part 300 is brought into contact with the skin simultaneously with the roller electrode members 200 by protruding to a height equal to that of the roller electrode members 200 or protruding to a height lower than the maximum protrusion height, the ball electrode part 300 may be maintained in a state in which the supply of the electric power is automatically cut off.

During a high frequency treatment, the roller electrode members 200 may be rubbed against the skin in one direction while being rotated in one direction, and the ball electrode member 320 may be rubbed against the skin in any direction while being freely rotated in a 360 degree radius.

Depending on the treated area and skin condition of the patient, the practitioner may perform the high frequency treatment in various manners. For example, the practitioner may rub the roller electrode members 200 in one direction against the treated area of the skin. Alternatively, the practitioner may protrude the ball electrode part 300 from the lower surface of the handpiece casing part 100 and then rub the roller electrode members 200 against the treated area while allowing the ball electrode member 320 to massage the skin. Alternatively, the practitioner may protrude the ball electrode part 300 to the maximum protrusion height from the lower surface of the handpiece casing part 100 and then freely rub the ball electrode member 320 in any direction against the treated area.

In other words, the high frequency treatment handpiece having roller electrodes according to the present disclosure may be used by selecting any one of a basic mode in which only the roller electrode members 200 are operated, a ball electrode mode in which only the ball electrode part 300 is operated, and a massage mode in which the roller electrode members 200 are operated while allowing the ball electrode part 300 to be brought into contact with the skin simultaneously with the roller electrode members 200.

On the other hand, the embodiment of the high frequency treatment handpiece having roller electrodes according to the present disclosure may further include: a display panel part 500 displaying treatment information such as intensity of high frequency applied during treatment, treatment time, and treatment mode on a screen; and a controller (not illustrated) connected to the display panel part 500 controlling the operation of the roller electrode members 200, the ball electrode part 300, and the electrode lifting part 400.

The display panel part 500 may be rotatably positioned on an upper surface of the stopper panel 410 and may be opened or closed for use.

The display panel part 500 is a touch screen panel that is operable by touch, allowing the practitioner to select and output necessary information and select the desired treatment mode by touching the panel.

The controller may include the basic mode in which only the roller electrode members 200 are operated, the ball electrode mode in which only the ball electrode part 300 is operated, and the massage mode in which the roller electrode members 200 are operated while allowing the ball electrode part 300 to be brought into contact with the skin simultaneously with the roller electrode members 200. During the treatment, any one of the basic mode, the ball electrode mode, and the massage mode may be selected through the display panel part 500.

Figure 6A:
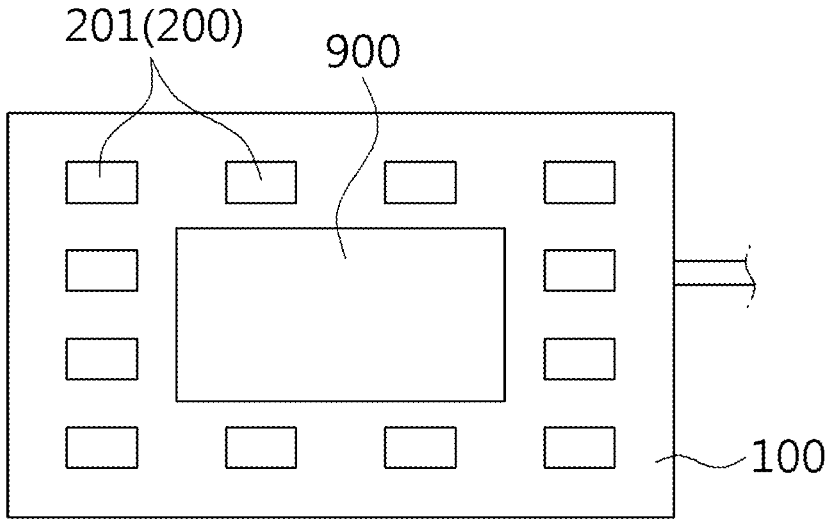
FIGS. 6(*a*) and 6(*b*) are bottom views illustrating another embodiment of a high frequency treatment handpiece having roller electrodes according to the present disclosure.
Figure 6B:
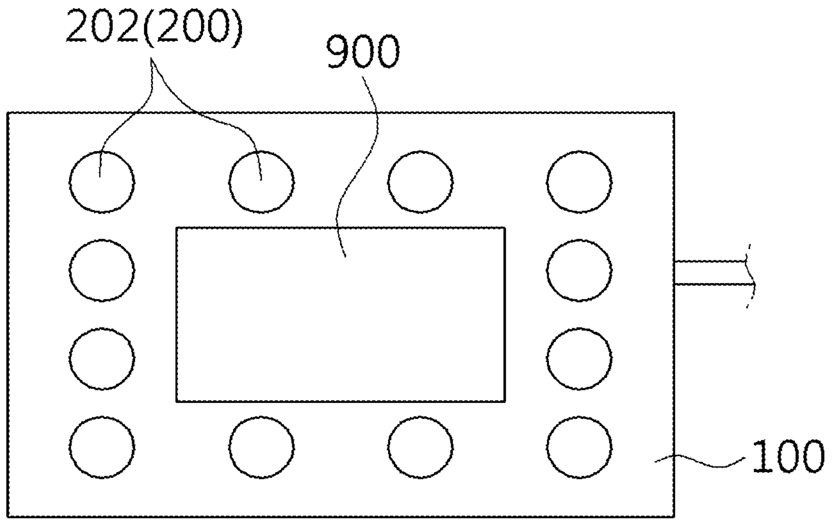
Figure 7A:
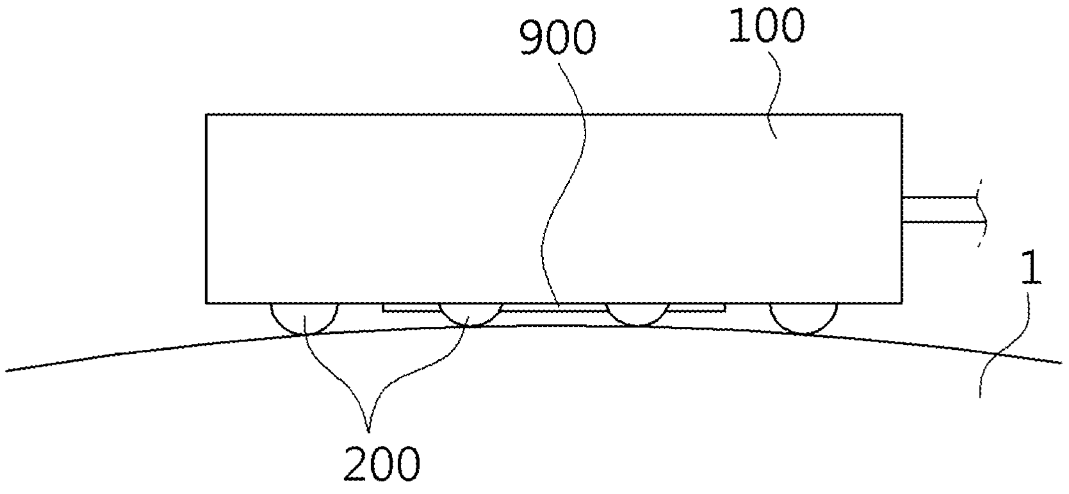
FIGS. 7(*a*) and 7(*b*) are use state views illustrating the other embodiment of the high frequency treatment handpiece having roller electrodes according to the present disclosure.
Figure 7B:
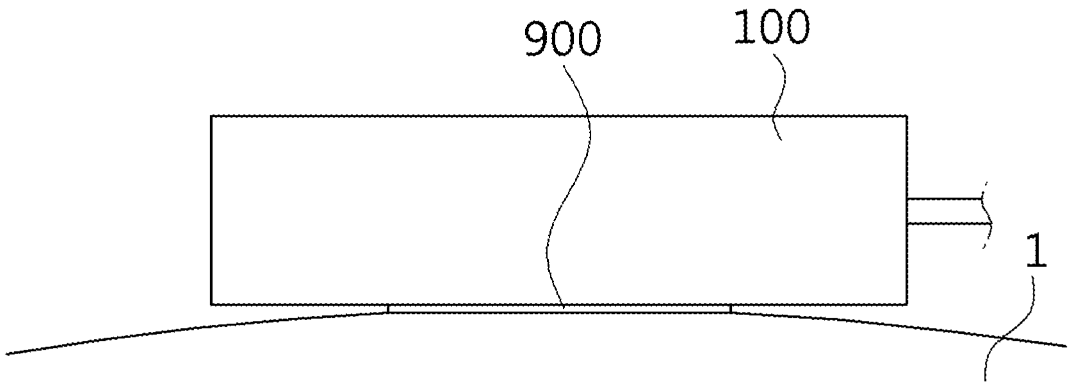

FIGS. 6(*a*) and 6(*b*) are bottom views illustrating another embodiment of a high frequency treatment handpiece having roller electrodes according to the present disclosure. FIGS. 7(*a*) and 7(*b*) are use state views illustrating the other embodiment of the high frequency treatment handpiece having roller electrodes according to the present disclosure.

Referring to FIGS. 6 and 7, the other embodiment of the high frequency treatment handpiece having roller electrodes according to the present disclosure may be configured such that a plurality of roller electrode members 200 are positioned to movable upward and downward in a handpiece casing part 100, and a flat electrode part 900 that is brought into contact with the skin 1 of a patient when the roller electrode members 200 are lifted may be positioned on a lower surface of the handpiece casing part 100.

As an example, the flat electrode part 900 is positioned at the center of the lower surface of the handpiece casing part 100 and the roller electrode members 200 are spaced apart from each other along the outer periphery of the flat electrode part 900.

The flat electrode part 900 is a Peltier element that cools the skin 1 to generate a cooling treatment effect on the skin 1, but the present disclosure is not limited thereto. For example, the flat electrode part 900 may be other known cooling treatment electrodes capable of cooling the skin 1.

The flat electrode part 900, i.e., the Peltier element, may be used for necrosis of fat cells by cooling the skin 1 to a low temperature of about 4° C.

FIG. 6(*a*) exemplarily illustrates that the roller electrode members 200 are roller-shaped electrodes 201, and FIG. 6(*b*) exemplarily illustrates that the roller electrode members 200 are ball-shaped electrodes 202. However, the present disclosure is not limited thereto, and various other shapes capable of being rotated and rolled in contact with the skin may also be used.

The roller electrode members 200 may be positioned to protrude from the lower surface of the handpiece casing part 100 in a state of being elastically supported by springs. Thus, the roller electrode members 200 may be inserted into the handpiece casing part 100 by being brought into contact with and pressed against the skin 1, allowing the flat electrode part 900 to be brought into contact with the skin 1.

In addition, although not illustrated in FIGS. 6 and 7, the embodiment of the high frequency treatment handpiece having roller electrodes according to the present disclosure may further include a roller lifting part lifting and lowering the roller electrode members 200. Thus, the roller electrode members 200 may be lifted by the operation of the roller lifting part and thereby inserted into the handpiece casing part 100, allowing the flat electrode part 900 to be brought into contact with the skin 1.

FIG. 7(*a*) illustrates that the roller electrode members 200 are lowered to a position protruding from the lower surface of the handpiece casing part 100 and perform a high frequency treatment while being rolled in contact with the skin 1. FIG. 7(*b*) illustrates that the roller electrode members 200 are lifted and inserted into the handpiece casing part 100 to allow the flat electrode part 900 to perform a cooling treatment in contact with the skin 1.

According to the high frequency treatment handpiece having roller electrodes according to the present disclosure, it is possible to perform the high frequency treatment through the roller electrode members 200 or to selectively perform the cooling treatment through the flat electrode part 900. In addition, by employing a structure in which the roller electrode members 200 are elastically supported by the springs, it is possible to allow the roller electrode members 200 and the flat electrode part 900 to be simultaneously brought into contact with the skin 1 by pressing the handpiece casing part 100, thereby simultaneously providing a high frequency treatment effect through the roller electrode members 200 and a cooling treatment effect through the flat electrode part 900.

Figure 8:
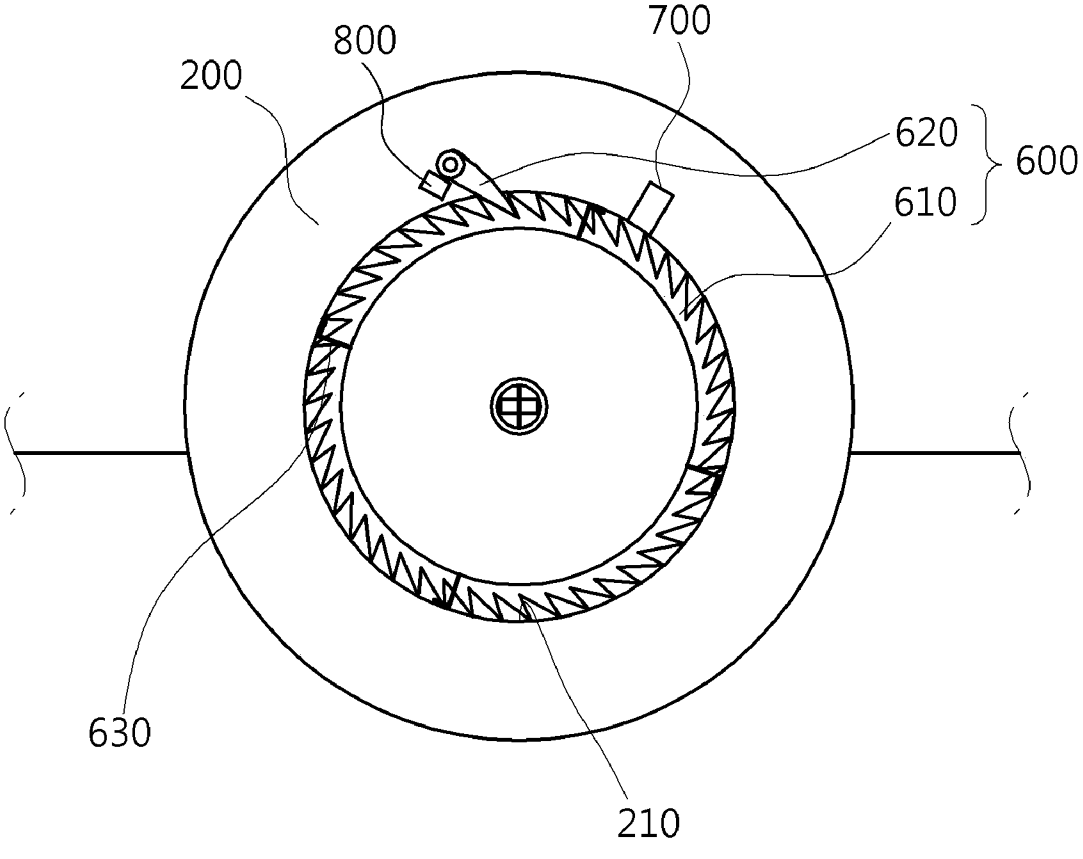
FIG. 8 is a schematic view illustrating an embodiment of a ratchet part of a roller electrode member in the embodiment of the high frequency treatment handpiece having roller electrodes according to the present disclosure.
Figure 9A:
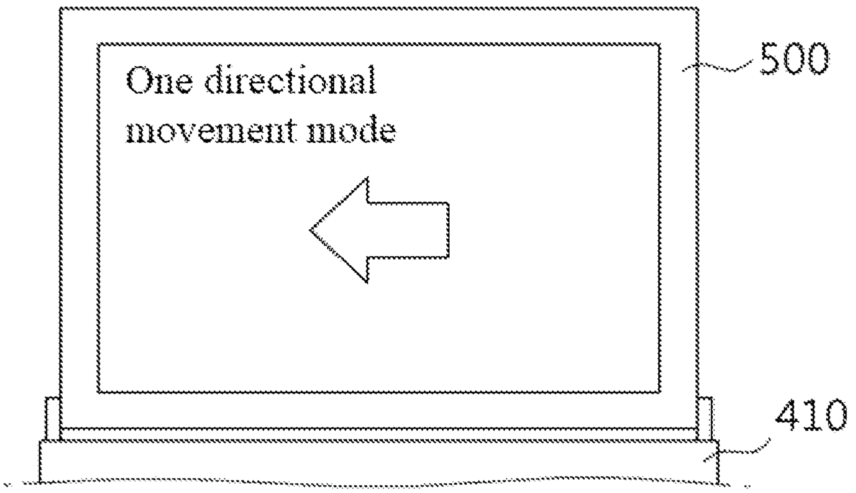
FIGS. 9(*a*) and 9(*b*) are views illustrating a screen displayed on a display panel part in the embodiment of the high frequency treatment handpiece having roller electrodes according to the present disclosure.
Figure 9B:
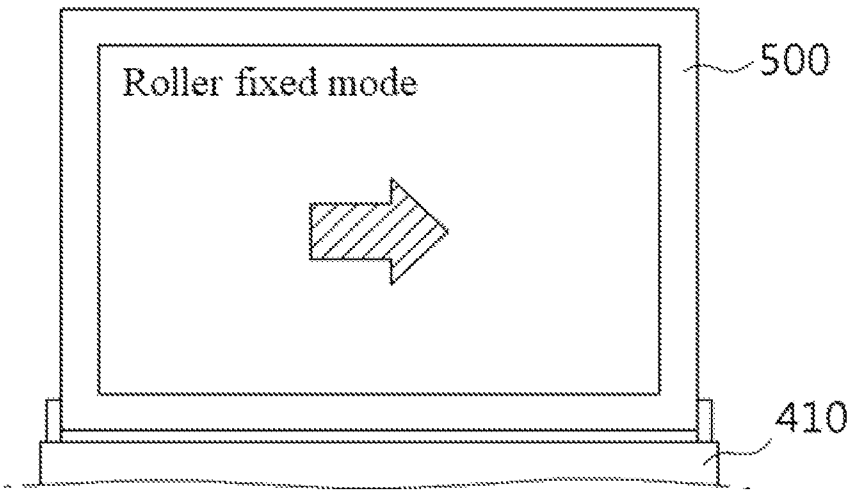

FIG. 8 is a schematic view illustrating an embodiment of a ratchet part 600 of each of the roller electrode members 200 in the embodiment of the high frequency treatment handpiece having roller electrodes according to the present disclosure. FIGS. 9(*a*) and 9(*b*) are views illustrating a screen displayed on the display panel part 500 in the embodiment of the high frequency treatment handpiece having roller electrodes according to the present disclosure.

Referring to FIGS. 8 and 9, the roller electrode member 200 may be rotated only in one direction by the ratchet part 600, and the controller may include a one direction movement mode and a roller fixed mode in the basic mode so that the one direction movement mode or the roller fixed mode is selected and used.

The ratchet part 600 includes: a ratchet wheel member 610 positioned in a hollow hole 210 of the roller electrode member 200 and on which the roller electrode member 200 is rotatably positioned; and a pawl member 620 positioned on the roller electrode member 200 and caught on outer teeth of the ratchet wheel member 610 in a state of being elastically supported by a spring so as to allow the roller electrode member 200 to rotate in one direction.

The roller electrode member 200 has the hollow hole 210 into which the fixed ratchet wheel member 610 is inserted, and is rotated around the ratchet wheel member 610 inserted into the hollow hole 210.

It should be noted that the ratchet wheel member 610 and the pawl member 620 are known ratchet mechanisms and a more detailed description will be omitted.

A power supply brush terminal 630 being in elastically contact with an inner circumferential surface of the hollow hole 210 and applying electric power to the roller electrode member 200 may be positioned on the ratchet wheel member 610.

A plurality of brush terminals 630 may be positioned in the circumferential direction of the ratchet wheel member 610 to stably apply electric power to the roller electrode member 200.

The embodiment of the high frequency treatment handpiece having roller electrodes according to the present disclosure may further include a rotation detection sensor 700 detecting the rotation of the roller electrode member 200.

The rotation detection sensor 700 may be a known sensor such as an inductive rotation speed sensor, a Hall sensor, etc., but the present disclosure is not limited thereto. Various other known sensors may also be used and a more detailed description thereof is omitted.

The embodiment of the high frequency treatment handpiece having roller electrodes according to the present disclosure may further include a pressure sensor 800 detecting the pressure applied to the pawl member 620 when the ratchet wheel member 610 is rotated in the reverse direction.

The roller electrode member 200 is allowed to be rotated only in one direction but limited from being rotated in the other direction by the ratchet part 600 to thereby perform the role of a fixed electrode.

The practitioner may select the one direction movement mode or the roller fixed mode through the display panel part 500.

When the one direction movement mode is selected, the display panel part 500 displays the rotation direction of the roller electrode members 200 with an arrow to guide the practitioner to move the handpiece casing part 100 in the moving direction indicated by the arrow.

The practitioner performs the treatment while moving the handpiece casing part 100 only in the moving direction indicated by the arrow in a state in which the roller electrode members 200 are in contact with the skin.

At this time, the roller electrode members 200 are rubbed against the skin while being rotated.

On the other hand, when the roller fixed mode is selected, the display panel part 500 displays the direction in which the roller electrode members 200 are not rotated, i.e., the direction in which the rotation thereof is limited by ratchet parts 600 with an arrow to guide the practitioner to move the handpiece casing part 100 in the moving direction indicated by the arrow.

The practitioner performs the treatment while moving the handpiece casing part 100 only in the moving direction indicated by the arrow in a state in which the roller electrode members 200 are in contact with the skin.

At this time, the roller electrode members 200 are rubbed against the skin while being fixed without rotation.

The rotation detection sensor 700 detects that the roller electrode members 200 are rotated in the roller fixed mode and transmits the detection result to the controller. The controller then notifies the practitioner that the roller electrode members 200 are rotated in the roller fixed mode, i.e., the moving direction of the handpiece casing part 100 in the roller fixed mode is incorrect, thereby allowing the practitioner to perform a correct treatment.

The pressure sensor 800 detects the pressure applied to pole members 620 when the roller electrode members 200 are about to be rotated in the reverse direction in the one direction movement mode and transmits the detection result to the controller. Then, the controller notifies the practitioner that the moving direction of the handpiece casing part 100 is incorrect in the one direction movement mode, thereby allowing the practitioner to perform a correct treatment.

The controller may notify the practitioner through the screen of the display panel part 500 that the moving direction of the handpiece casing part 100 is incorrect, or notify the practitioner by outputting a voice through a speaker, but the present disclosure is not limited thereto. Various other known notification means may also be used and a more detailed description thereof is omitted.

By the provision of the roller electrodes that are rotated in contact with the skin, the present disclosure prevents burning when the continuous rubbing of the treated area is performed during a treatment, allows the practitioner to conveniently perform the treatment, and allows the person being treated to comfortably receive the treatment with minimum pain.

The ball electrodes and roller electrodes can be selectively used, and the roller fixed mode, which limits the rotation of the roller electrodes, can also be selectively used. Thus, various massage effects can be selectively provided in accordance with the condition of the patient's skin, and the effect of the high frequency treatment can be maximized by means of the various massage effects.

The present disclosure is not limited to the above-described embodiment, and various modifications can be made without departing from the scope of the present disclosure, which is intended to be defined by the appended claims.

The invention claimed is:

1. A high frequency treatment handpiece having roller electrodes, the high frequency treatment handpiece comprising:

a handpiece casing part; and a plurality of roller electrode members rotatably positioned on a lower surface of the handpiece casing part and configured to apply a high frequency by being brought into contact with a skin of a patient, wherein the plurality of roller electrode members are selectively used in a roller fixed mode that limits a rotation and a one direction movement mode, and the plurality of roller electrodes members are rotated only in one direction by a ratchet part, wherein the ratchet part includes:

a ratchet wheel member positioned in a hollow hole of the plurality of roller electrode members and on which the plurality of roller electrode members are rotatably positioned, and a pawl member positioned on the plurality of roller electrode members and caught on outer teeth of the ratchet wheel member in a state of being elastically supported by a spring so as to allow the plurality of roller electrode members to rotate in one direction.

2. The high frequency treatment handpiece of claim 1, further comprising:

a ball electrode part positioned to be movable upward and downward in the handpiece casing part and having a ball electrode member that protrudes from a lower surface thereof, configured to be rolled in contact with the skin, and configured to apply a high frequency; and an electrode lifting part configured to move the ball electrode part upward and downward.

3. The high frequency treatment handpiece of claim 2, wherein the ball electrode part is positioned to protrude from the lower surface of the handpiece casing part so that the ball electrode member is positioned to protrude to a height equal to or lower than a height of the roller electrode members, whereby when the roller electrode members are brought into contact with the skin, the ball electrode member is brought into contact with the skin simultaneously with the roller electrode members and is rolled in contact with the skin to generate a massage effect on the skin.

4. The high frequency treatment handpiece of claim 3, wherein the ball electrode member is positioned to protrude from the lower surface of the handpiece casing part so that when the ball electrode member is brought into contact with the skin simultaneously with the roller electrode members, the ball electrode member is in a state in which the supply of electric power is cut off.

5. The high frequency treatment handpiece of claim 3, wherein the electrode lifting part comprises a stopper panel connected to the ball electrode part, positioned to be spaced apart from an upper portion of the handpiece casing part, and configured to limit a maximum protrusion height of the ball electrode part, wherein the maximum protrusion height of the ball electrode part limited by the stopper panel is a height at which only the ball electrode member applies the high frequency by being brought into contact with the skin while the roller electrode members are not brought into contact with the skin.

6. The high frequency treatment handpiece of claim 5, wherein a first ball electrode power application terminal configured to apply electric power to the ball electrode part is positioned on a lower surface of the stopper panel, and a second ball electrode power application terminal electrically connected to the first ball electrode power application terminal and configured to apply electric power to the ball electrode part is positioned on an upper surface of the handpiece casing part, wherein when the ball electrode part protrudes to the maximum protrusion height from the lower surface of the handpiece casing part as the stopper panel is seated on the upper surface of the handpiece casing part, the ball electrode part applies the high frequency to the skin through electrical connection between the first and second ball electrode power application terminals.

7. The high frequency treatment handpiece of claim 1, wherein the plurality of roller electrode members are positioned to be movable upward and downward in the handpiece casing part, and a flat electrode part configured to be brought into contact with the skin of the patient when the roller electrode members are lifted is positioned on the lower surface of the handpiece casing part.

8. The high frequency treatment handpiece of claim 7, wherein the roller electrode members are positioned to protrude from the lower surface of the handpiece casing part in a state of being elastically supported by springs so that the roller electrode members are inserted into the handpiece casing part by being brought into contact with and pressed against the skin, allowing the flat electrode part to be brought into contact with the skin, or a roller lifting part configured to lift and lower the roller electrode members is further provided so that the roller electrode members are lifted by the operation of the roller lifting part.

9. The high frequency treatment handpiece of claim 7, wherein the roller electrode members are roller-shaped electrodes or ball-shaped electrodes, and the flat electrode part is a Peltier element that is configured to cool the skin to generate a cooling treatment effect on the skin.

* * * * *